United States Patent [19]

Deshpande et al.

[11] Patent Number: 5,147,634
[45] Date of Patent: Sep. 15, 1992

[54] HEAT GENERATING PERMANENT WAVING COMPOSITION

[75] Inventors: Vikas M. Deshpande, Ringwood, N.J.; John M. Walts, Shohola, Pa.

[73] Assignee: Eastman Kodak Company, Rochester, N.Y.

[21] Appl. No.: 651,869

[22] Filed: Feb. 7, 1991

[51] Int. Cl.⁵ .......................... A61K 7/07; A61K 7/09
[52] U.S. Cl. ...................................... 424/70; 424/71; 424/72; 132/203; 132/204; 132/209
[58] Field of Search .................... 424/71, 72; 132/203, 132/204, 209

[56] References Cited

U.S. PATENT DOCUMENTS

| | | | |
|---|---|---|---|
| 2,836,185 | 5/1958 | Hervey | 424/70 |
| 3,567,363 | 3/1971 | Wolfram | 424/72 X |
| 3,864,476 | 2/1975 | Altieri | 424/70 |
| 3,865,930 | 2/1975 | Abegg et al. | 424/72 |
| 4,296,764 | 10/1981 | Pallone et al. | 424/70 |

FOREIGN PATENT DOCUMENTS 2066864 7/1981 United Kingdom ................ 132/203

Primary Examiner—Thurman K. Page
Assistant Examiner—Sally Gardner
Attorney, Agent, or Firm—John R. Everett

[57] ABSTRACT

A heat generating hair permanent composition is disclosed. The composition has a pH of about 6.8 to 10. It is the reaction product of a mixture of about 6 to 10 parts of an aqueous hair reducing composition containing from 5 to 20 weight percent reducing agent with about 0.5 to 3 parts of an aqueous oxidizing solution which contains 1 to 6 weight percent hydrogen peroxide.

10 Claims, No Drawings

HEAT GENERATING PERMANENT WAVING COMPOSITION

FIELD OF THE INVENTION

The present invention relates to compositions for waving or straightening hair.

BACKGROUND OF THE INVENTION

Chemical compositions for use in the permanent or cold waving and straightening of hair are known. Among these are alkaline and neutral compositions containing a bisulphite or sulfite compound. Such compositions are disclosed in U.S. Pat. Nos. 2,836,185 and 3,864,476 and British Patent 849,045.

U.S. Pat. No. 4,296,764 discloses a hair waving and straightening process that involves treating the hair with a reducing agent followed by treatment with hydrogen peroxide as a neutralizer. The problem is that the reducing agent must be maintained in contact with the hair 30 to 120 minutes. The period can be shortened by the application of external heat.

SUMMARY OF THE INVENTION

The above problem is greatly ameliorated by the present invention which provides a heat generating hair permanent composition having a pH of about 6.8 to 10 and which is the reaction product of a mixture of about 6 to 10 parts of an aqueous hair reducing composition containing from 5 to 20 weight percent reducing agent with about 0.5 to 3 parts of an aqueous oxidizing solution containing 1 to 6 weight percent hydrogen peroxide.

In a particularly useful embodiment the present invention provides a heat generating hair permanent composition having a pH of about 7.1 to 7.7, preferably 7.5, and which is the reaction product of a mixture of about 7 to 9 parts, preferably 8 parts, of an aqueous hair reducing composition containing about 13.0 to 15.0, preferably 14, weight percent reducing agent with about 1.5 to 3, preferably 2, parts of an aqueous oxidizing solution containing about 3 to 5, preferably, 4.5 weight percent hydrogen peroxide.

It is essential that the composition have a pH in the range 6.8 to 10 to achieve the desired straightening or waving. In the context of this specification the term "hair permanent" includes hair waving, curling and straightening.

The composition contains no residual hydrogen peroxide in the reaction product.

This unique formulation does not contain mercaptan compounds as in more conventional permanent waving solution. Such compounds emit strong unpleasant odors and may damage hair if improperly used or used too often.

The heat generated by the hair permanent of this invention provides even and complete processing of hair in about one-half the time required with conventional cold sulfite/bisulfite hair permanents. Surprisingly the permanent of this invention does not require the high pH treatment to effect hydrogen peroxide neutralization normally required with some cold sulfite/bisulfite hair permanents. Moreover this invention has the advantage that reduction of hair at neutral pH is more efficient than at high pH. This avoidance of exposure of hair to high pH is expected to leave the hair in a superior condition.

DETAILS OF THE INVENTION

The composition of the invention can be readily used professionally or for home application for either straightening, curling or waving hair. The heat generating composition provides truly elastic, sleek straightened, curl or waved hair. This composition can be used without using a neutralization step by simply rinsing with water to remove $HSO_3-$ and $SO_3-$ and exposing the hair to air. Optionally it can also be used in conjunction with a neutralizing step.

The novel heat generating hair permanent composition is made in two parts, part A (reducing or permanenting composition) and part B (heat activator composition). Parts A and B can be supplied to the consumer in the form of a kit with each part in its own package such as bottles or tubes. When parts A and B are mixed in proper ratio as required by the present invention, an exothermic reaction occurs. The temperature of the resulting composition rises 16 to 20 degrees centigrade above ambient room temperature. When this mixture is applied to hair it provides deep, even, complete processing. After application and during hair processing the hair can be covered with a fitted plastic cap to help maintain the elevated temperature of the mixture. The use of a plastic cap is optional. With the composition of this invention hair processing is easily controlled and gentle to the hair. The composition can be used with or without conventional oxidant neutralizers. The neutralizer can be cold or heat activated.

Table I provides typical formulations for part A and part B.

TABLE I

Part I:
Formula examples based upon the increase in heat after mixing two components (Part A & B) and giving 16°-20° C. temperature rise from the ambient room temperature.

| Ingredient | % w/w | % w/w | Function |
|---|---|---|---|
| Part A - Composition | | | |
| Water | Q.S. to 100 | Q.S. to 100 | Vehicle |
| Sodium Bisulfite | 10-18% | — | Reducing agent |
| Ammonium Bisulfite, 45% | — | 22.2-45% (10-18% w/w) | Reducing agent |
| TEA Cocohydrolyzed Animal Protein | 0.5-2% | 0.5-2% | Protein Conditioner |
| Ethanolamine | Q.S. to pH 6.8-10 | Q.S. to pH 6.8-10 | Alkalizing agent |
| Urea | 5-15% | 5-15% | Penetrating agent |
| Sodium Carbonate | 0.5-3.5% | — | Buffer |
| Lactamide MEA | — | 1-2% | Moisturizer |
| Ammonia, 26% | — | Q.S. to pH 6.8-10 | Alkalizing agent |
| Part B - Heat Activator | | | |

TABLE I-continued

Part I:
Formula examples based upon the increase in heat after mixing two components (Part A & B) and giving 16°-20° C. temperature rise from the ambient room temperature.

| Ingredient | % w/w | % w/w | Function |
|---|---|---|---|
| Water | Q.S. to 100 | | Vehicle |
| Methylparaben | 0.05 | | Preservative |
| Hydrogen Peroxide, 35% w/w | 8.5–16% (3–5.6% w/w) | | Oxidizing agent |
| Disodium phosphate | 0.02 | | Buffer |
| Phosphoric Acid, 85% | Q.S. to pH 3.0–4.5 | | to adjust pH |

The hair is straightened or waved using the following process. First the hair is cleaned by shampooing and left damp. The hair is wrapped on rods or curlers if hair waving and/or curling is desired. If straightening is desired the reducing composition may simply be applied directly to the hair and combed through the hair. The composition resulting from the mixture of parts A and B described above is applied to the hair all around the rods or rollers. The composition is kept in contact with the hair for about 20 to 40 minutes for normal, resistant or fine hair and 10 to 30 minutes for color treated or lightly frosted hair. The hair is then rinsed with warm water with the curlers or rods still in place. Optionally, a conventional neutralizer can be now applied to the hair. If so, the neutralizer is applied to the hair thoroughly and then rinsed out.

Useful reducing agents for part A include acidic metal sulfites and bisulphites, e.g. sodium bisulphite and/or sulfite, potassium bisulphite and/or sulfite, and/or potassium meta-bisulphite or ammonium bisulfite and/or sulfite. Other useful reducing agents are disclosed in U.S. Pat. Nos. 2,836,185 and 3,864,476 and British patent 849,045. When waving or straightening hair with alkali bisulphite and/or sulfite preparations, disulfide and hydrogen bonds as well as various salt, linkages within the hair are broken. Optionally the broken bonds in the newly waved or straightened position can be locked in and set with the use of conventional oxidizing neutralizers. However application of such neutralizers is unnecesary since air oxidation is entirely sufficient.

Alkalizing agents such as alkanolamines are used in part to obtain the required pH, both in part A and in the composition resulting from the mixture of part A with part B. Useful alkanolamines include monoethanolamine, diethanolamine, triethanolamine, isopropanolamine, diisopropanolamine and mixtures thereof. The alkanolamine is employed at a concentration of from about 0.05 to 5% by weight. Ammonia can also be used to obtain the required pH.

In order to maintain the pH in those compositions which use alkali metal bisulfite and sulfite reducing agents it is necessary to include a buffering agent. Useful buffering agents include alkali metal carbonates such as sodium, or potassium carbonate; and alkali metal phosphates such as mono-, di-, or tri-sodium or potassium phosphate or mixtures of such buffers.

When ammonium bisulfite is the reducing agent of choice it has been found that a buffering agent may be omitted since such compositions are self-buffering. However, carbonate and phosphate buffers may be used if desired. The concentration used is from about 0.5 to 3.3% by weight.

It is advantageous to include in the composition TEA-coco-hydrolyzed animal protein (CFTA adopted name) as a conditioner. This chemical is the triethanolamine salt of the condensation product of coconut acid chloride and hydrolyzed animal protein. It is used in a concentration of from about 0.5 to 2.0% by weight.

The composition of the invention may include effective amounts of optional ingredients in order to impart additional desirable properties and/or aesthetic appeal to the composition such as additional hair conditioners, preservatives, moisturizers, etc.

Useful preservatives include methylparaben, ethylparaben or propylparaben. They be used in concentrations of from about 0.05 to 0.3% by weight.

Useful moisturizers include lactamide MEA (CFTA adopted name) which is lactic acid monoethanolamide.

The invention has been described in detail with particular reference to preferred embodiments thereof, but it will be understood that variations and modifications can be effected within the spirit and scope of the invention.

We claim:

1. A heat generating hair permanent composition having a pH of about 6.8 to 10, contains no residual hydrogen peroxide and is the reaction product of a mixture of (a) about 6 to 10 parts of an aqueous hair reducing composition containing from 5 to 20 weight percent of a reducing agent selected from the group consisting of sulfites, bisulfites or a mixture of both and (b) with about 0.5 to 3 parts of an aqueous oxidizing solution which contains 1 to 6 weight percent hydrogen peroxide.

2. A heat generating hair permanent composition according to claim 1 having a pH of about 7.1 to 7.7 and which is the reaction product of a mixture of about 7 to 9 parts of an aqueous hair reducing composition containing from 13.0 to 15.0 weight percent reducing agent with about 1.5 to 3.0 parts of an aqueous oxidizing solution which contains 3 to 5 weight percent hydrogen peroxide.

3. A heat generating hair permanent composition according to claim 1 having a pH of about 7.5 and which is the reaction product of a mixture of about 8 parts of an aqueous hair reducing composition containing about 14 weight percent reducing agent with about 2 parts of an aqueous oxidizing solution containing about 4.5 weight percent hydrogen peroxide.

4. The composition of claim 2, 3 or 1 wherein the hair reducing agent is an ammonium or an alkali metal a) bisulfite, b) sulfite or a mixture of both.

5. The composition of claim 2, 3 or 1 wherein the reducing agent is sodium bisulfite, ammonium bisulfite or mixtures thereof.

6. A hair permanent kit comprising two separate packages wherein one package includes an aqueous composition having a pH of 6.8 to 10 and contains from 5 to 20 weight percent of a hair reducing agent selected from the group consisting of sulfites, bisulfites or a mixture of both and the other package includes an aqueous oxidizing composition having a pH of a 3.0 to 4.5 and which contains 1 to 6 weight percent; provided that a mixture of the contents of the two packages contains no residual hydrogen peroxide.

7. The kit of claim 6 wherein one package contains an aqueous hair reducing composition having a pH of about 7.1 to 7.7 and includes about 7 to 9 parts of reducing agent and the other package contains an aqueous oxidizing solution containing about 3 to 5 parts weight percent hydrogen peroxide.

8. The kit of claim 6 wherein one package contains an aqueous hair reducing composition having a pH of about 7.5 and includes about 14 weight percent reducing agent and the other package contains an aqueous oxidizing solution containing about 4.5 weight percent hydrogen peroxide.

9. The kit of claim 6, 7, or 8 wherein the hair reducing agent is an ammonium or an alkali metal a) bisulfite, b) sulfite or a mixture of both.

10. The kit of claim 6, 7, or 8 wherein the reducing agent is sodium sulfite or ammonium sulfite or mixtures thereof.

* * * * *